United States Patent [19] [11] 3,959,765
Stewart [45] May 25, 1976

[54] STOICHIOMETRIC AIR/FUEL RATIO EXHAUST GAS SENSOR

[75] Inventor: Karen L. Stewart, Woodhaven, Mich.

[73] Assignee: Ford Motor Company, Dearborn, Mich.

[22] Filed: Sept. 2, 1975

[21] Appl. No.: 609,768

[52] U.S. Cl. .................................................. 338/34
[51] Int. Cl.² .......................................... H01C 13/00
[58] Field of Search ............ 73/23, 27 R; 23/254 E, 23/255 E; 338/34

[56] References Cited
UNITED STATES PATENTS
2,926,520   3/1960   Schmauch ........................ 73/27 R
3,911,386   10/1975  Beaudoin et al. .................... 338/34

Primary Examiner—James J. Gill
Attorney, Agent, or Firm—Keith L. Zerschling; Robert A. Benziger

[57] ABSTRACT

A stoichiometric air/fuel ratio exhaust gas sensor construction particularly useful with variable resistance partial pressure of oxygen responsive sensor material is disclosed. A generally cylindrical mounting body, formed of corrosion resistant material, is arranged for receipt within the exhaust system of an internal combustion engine and is provided with a ceramic insert member for support of a wafer of variable resistance sensor material. The ceramic insert member is comprised of an extending first portion having a hollow slotted tip for receipt and support of the wafer of partial pressure of oxygen responsive ceramic sensor material. The extending first portion of the ceramic insert member is arranged to position the wafer within, and extending from, a remote free end of the cylindrical housing body. The wafer includes a pair of extending high temperature resistant electrical conductors which are received within bores provided therefor in the extending first portion of the ceramic insert member. The wafer leads are electrically connected by a glass seal material to a pair of electrically low resistance, high temperature resistant relatively rigid connector pins which are received within a pair of passages extending from the rear face of the ceramic insert member and intersecting the wafer conductor passages.

10 Claims, 6 Drawing Figures

RICH ~14.7 LEAN
STOICHIOMETRY
AIR/FUEL MIXTURE

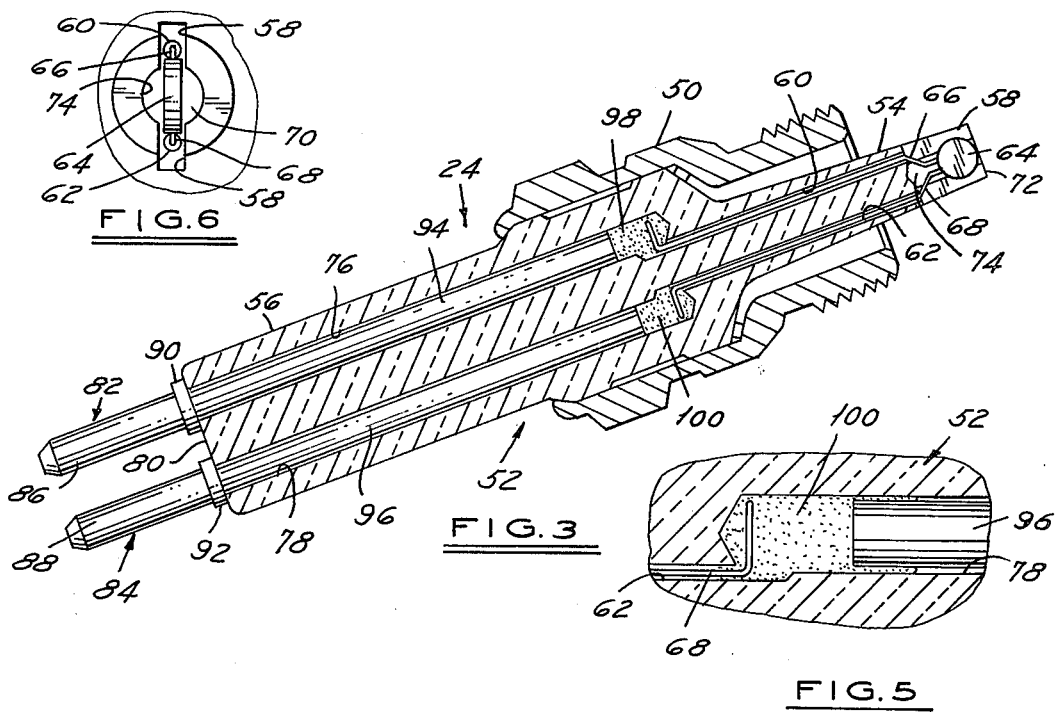
FIG. 6
FIG. 3
FIG. 5
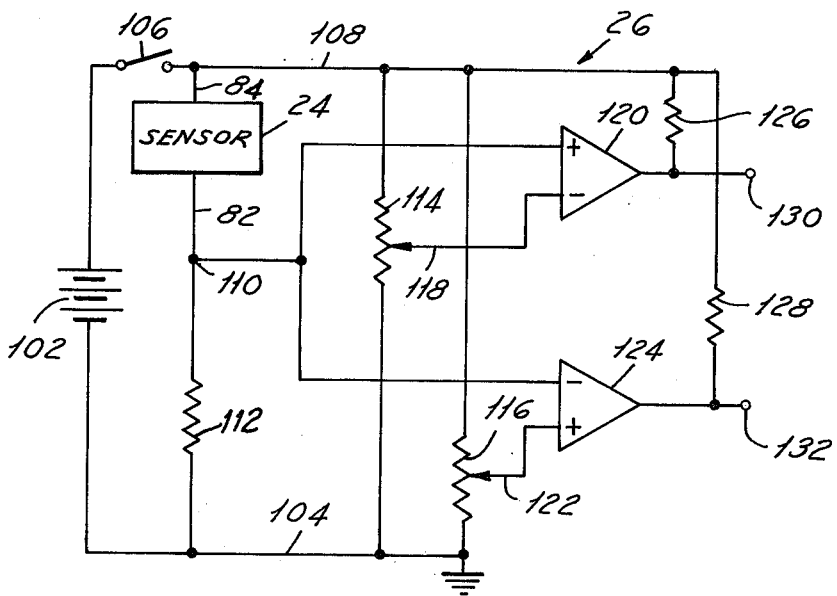
FIG. 4

STOICHIOMETRIC AIR/FUEL RATIO EXHAUST GAS SENSOR

CROSS REFERENCE TO RELATED APPLICATIONS

The present invention is related to the subject matter described in copending, commonly assigned patent application Ser. No. 609,767 for Stoichiometric Air/Fuel Ratio Exhaust Gas Sensor filed Sept. 2, 1975 in the names of Michael J. Esper et al.

BACKGROUND OF THE INVENTION

1. Field of the Invention

The present invention is directed to the field of exhaust gas chemistry responsive sensors. More particularly, the present invention is directed to that portion of the above-noted field which is concerned with the construction of an exhaust chemistry responsive sensor for insertion in the exhaust system of an automotive internal combustion engine to provide a signal indicative of the air to fuel ratio of the combustion mixture producing the exhaust gases. More particularly still, the present invention is directed to that portion of the above-noted field which is concerned with the provision of an exhaust gas sensor which may be used to indicate a condition of stoichiometry in the combustion mixture which is generating the exhaust gases as a byproduct of combustion and which sensor may be used as an input device for an air/fuel ratio controller such that the combustion mixture may be maintained at stoichiometry. More particularly still, the present invention is directed to that portion of the above-noted field which is concerned with providing an exhaust gas chemistry responsive sensor which will be substantially lower in cost and of substantially less complexity, while being rugged and durable, than prior exhaust gas sensors.

2. Description of the Prior Art

There are generally speaking, two classes of exhaust gas sensors. Each makes use of a material which responds principally to the partial pressure of oxygen in the exhaust gases. The first of these, which is exemplified by the use of zirconia as the operative material, responds to a differential partial pressure of oxygen between a reference source of gas and a gas being sensed to generate a galvanic voltage or electromotive force between the surfaces of the material which are exposed to the two gases. This generated voltage may be used as a signal. These devices require that the surfaces exposed to the gases be provided with porous electrodes and that one surface be exposed to a relatively constant reference source while the second surface is exposed to the exhaust gases. This requirement presents constructional problems since it is normally the practice to use ambient air as the reference gas. This introduces substantial temperature gradients across the ceramic material. In order to provide rapid response times and for various other desirable operating characteristics, the zirconia material is preferably kept thin. The above-noted requirement and the preferred thinness also present sealing problems as well as other problems of an electrical nature. As a result, this class of devices tends to be fragile, expensive and relatively unreliable after being in use for a term of time less than that required to give an average of about 50,000 driving miles of service.

A second group of exhaust gas chemistry responsive sensors, which may be typified by the use of for example titania ceramic material as the operative material, exhibits an electrical resistance resistance which varies, at elevated temperatures, as a function of the partial pressure of oxygen in the gaseous environment of the ceramic and as a function of temperature. U.S. Pat. No. 3,886,785 describes a titania ceramic exhaust gas sensor configuration which utilizes an electrical heat source to provide the sensor with an initial heating and to thereafter maintain the sensor at a specific selected elevated temperature so that resistance variations will not be caused by fluctuations in the exhaust temperature.

Electrical heating means are typically provided in the form of an electrical resistance coil formed of platinum conductive wire. Such a heat source contributes substantially to the cost of a sensor, both from the standpoint of the cost of the platinum material and from the standpoint of the manufacturing complexity presented by the necessity of mounting the heater and communicating the heater, through the support ceramic material, to a separate electrical source for energization. Precise temperature control is required to eliminate temperature variations from influencing the sensor signal and to provide a very accurate temperature control particularly for operation of the associated internal combustion engine at nonstoichiometric combustion mixture ratios.

Investigation of the electrical resistance versus air/fuel ratio response curve of titania exhaust gas sensors has indicated that the resistance value of the titania varies substantially for the exhaust by-products of combustion mixtures which experience a lean to rich or rich to lean excursion or transition. In many instances, this variation may be several orders of magnitude, even in the face of adverse temperature variations. It is therefore an object of the present invention to provide a titania-based exhaust gas partial pressure of oxygen sensor to operate in the exhaust system of an internal combustion engine operated with a combustion mixture having a stoichiometric air/fuel ratio which is low in cost and relatively simple to assemble.

One continuing objective which the automotive industry in general has in fabricating any power train related component is maximum durability. The federal law has further stimulated the automotive industry to attempt to obtain, in the case of pollution control related engine components such as an exhaust gas sensor for use in a feedback air/fuel ratio control system, a durability factor which would be equivalent to operation of the average vehicle over approximately 50,000 miles. Under such a requirement, an exhaust gas sensor would be required to undergo a large number of thermal cycles and considerable vibration as well as being required to withstand the extremes of seasonal weather contaminates to which a vehicle may be subjected. Such a device, in order to be cost effective, would have to achieve the desired level of operation and reliability while maintaining as low a cost as possible. Since the sensor and its associated mechanical hardware would be subjected to the high temperature environment of the exhaust system and could be expected to be subjected to exposure to road salt and the like it would be necessary that the electrical portion of the sensor be capable of withstanding thermal cycling in the presence of salt environment. Conventional low cost means of thermal and environmental insulation would not normally be expected to hold up to this type of environment and the number of electrical leads associated with the exhaust gas sensor would multiply the statistical chances of failure. It is therefore a further and specific object of the present invention to provide an exhaust gas chemistry responsive sensor requiring only a pair of electrical leads which may be arranged in such a fashion as to assure maximum protection against salt, road spray, and splash. While various of these objectives have been achieved with the sensor construction according to the prior art and particularly with the above-noted copending, commonly assigned patent application Ser. No. 609,767 the reduction of cost without incurring performance or operational sacrifices is a continuing objective. It is therefore a further and specific objective of the present invention to provide a low cost, low complexity exhaust gas sensor of the variable resistance type to operate as a stoichiometry indicator in an exhaust gas feedback responsive air/fuel ratio controller. More particularly still, it is an object of the present invention to provide an exhaust gas sensor of rugged construction which is low in cost and which is of sufficiently simple construction that it may be manufactured on largely automated machinery.

The above-noted copending, commonly assigned patent application Ser. No. 609,767 sets forth the desirability of providing an exhaust gas sensor construction in which the electrical connection between the resistive type sensor material leads (the wafer leads) and the electrical connector which will communicate variations in sensor resistance as an input parameter to a feedback operated air/fuel ratio control fuel system be made at a location which is interior to the sensor device. According to the construction there described, a two-piece ceramic insert member is provided to allow convenient access to the interior of the sensor device so that the electrical interconnection may be conveniently and realiably accomplished. The sensor construction according to this prior art teaching has achieved significant cost savings by reducing the amount of precious metal, platinum, conductor to an absolute minimum in the sensor configuration but has, unfortunately, added a degree of complexity to the manufacturing operation occasioned by use of a two-piece ceramic insulator.

Since the reduction of components ordinarily carries with it a reduction in cost and manufacturing complexity, it is therefore a further and specific object of the present invention to provide an exhaust gas sensor construction which utilizes a one-piece ceramic insert member but which maintains the electrical interconnection between the sensor leads and the electrical terminal conductor at a point which is interior to the sensor device. More specifically, it is a specific object of the present invention to provide an exhaust gas sensor construction in which the electrical interconnection between the precious metal sensor lead and the electrical terminal conductors may be accomplished interiorly of the ceramic insert member.

Partial pressure of oxygen responsive sensors of both classes have required the provision of shield means to prevent the direct impingement of the exhaust gases upon the sensor material. This is necessary since pressure pulsations exist within the exhaust gas and the pulsations would quickly produce fractures within the thin ceramic material if directly exposed to the exhaust gas stream. According to the prior art, an apertured or perforated cylindrical body of corrosion resistant material is arranged to extend from the housing or outer body. This shield member is typically formed of a metal such as stainless steel or is a simple extention of the metallic outer body. In either event, the shield member has limited useful life due to the highly corrosive atmosphere of the exhaust gas and adds expense to the cost of the sensor device. It is therefore an object of the present invention to provide nonmetallic shield means for the sensor wafer.

SUMMARY OF THE PRESENT INVENTION

The present invention provides an exhaust gas chemistry responsive sensor device having a metallic outer body adapted for threaded connection to a suitable land or boss on the exhaust system of an internal combustion engine for inserting and supporting a wafer of variable resistance exhaust gas chemistry responsive material into the exhaust system. The sensor device includes a ceramic body insert member having a first extending portion which is slotted and counter-bored at a remote end and which has a pair of internally extending passages for receipt of the electrical leads, typically formed of a precious metal such as platinum, from the sensor wafer. The sensor wafer is received in supported fashion within the slotted and counter-bored end portion of the first portion of the ceramic body. The ceramic insert member or insulator means includes a second, generally cylindrical, portion which is aligned with the first portion and includes a pair of enlarged passages which intercommunicate the wafer lead passages with the rear face of the ceramic insulator means. The ceramic insulator means is sealingly received within the metallic outer body. One each of a pair of relatively rigid conductive leads or pin members is received within each of the enlarged passages of the second portion of the ceramic insulator means and extends into proximity with the wafer lead passages provided in the first portion of the insulator means. The remote free ends of the connector pins are formed as male connectors for receipt within female connectors of an electrical connector block. The interiorly situated end of each connector pin is electrically communicated to a corresponding one of said pair of wafer leads with said intercommunication being interior to the ceramic insulator means and generally proximate to the junction between the first and second portions of the ceramic insert member. The electrical interconnection is accomplished by means of conductive glass seals which provide for good electrical properties while providing gas-tight seals of good mechanical strength and compatibility with the ceramic and with the temperatures of operation.

In manufacture, the sensor chip is positioned within the slotted end of the first portion of the ceramic insulator member while the wafer electrical leads are received within the passages provided therefor within the first portion of the insulator means. The ceramic insulator means is deposited within a suitable holder or fixture for example in suspended relation. With the wafer retained within the counter bore at the end of the ceramic insulator means, the free ends of the wafer leads are crimped over the shoulders situated at the intersections of the wafer lead passages and the enlarged passages. A charge of conductive glass is deposited within each of the enlarged passages. Heat is applied to the ceramic insulator to bring the glass charge to molten temperature and two pin members are fed through the enlarged passages provided therefor in the second portion of the ceramic insert member and are forcibly inserted into the glass charge. The ceramic insulator means is thereafter allowed to cool to permit the molten conductive glass material to establish a mechanically strong and electrically highly conductive interconnection between the sensor wafer leads and the connector pin members. The composite structure is thereafter provided with suitable seal means and inserted into the metallic outer body which is then crimped to maintain the ceramic insulator means in tightly sealed relation with respect to the outer body.

BRIEF DESCRIPTION OF THE DRAWINGS

FIG. 3 illustrates a sectional view of the exhaust gas chemistry responsive sensor apparatus according to the present invention.

FIG. 4 illustrates one representative electrical circuit which may respond to the sensor apparatus of FIG. 3 to provide an output signal for controlling the air/fuel ratio controller illustrated in FIG. 1.

FIG. 5 is an enlarged sectional view of a portion of the sensor apparatus as shown in FIG. 3 illustrating one feature of the present invention.

FIG. 6 is an enlarged fragmentary end view of sensor apparatus of FIG. 3 illustrating one feature of the present invention.

DETAILED DESCRIPTION OF THE PREFERRED EMBODIMENT

Figure 1:
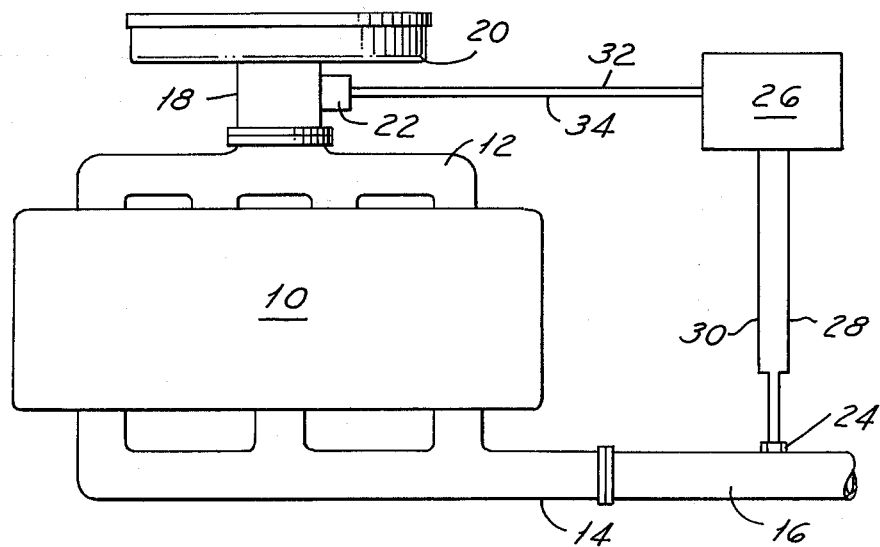
FIG. 1 is a schematic diagram illustrating an internal combustion engine having an exhaust responsive feedback air/fuel ratio control mechanism with which the present invention is of utility.

Referring now to FIG. 1, an internal combustion engine 10 is illustrated. Internal combustion engine 10 is provided with an intake manifold 12 and an exhaust manifold 14. Exhaust manifold 14 communicates with an exhaust gas conduit 16. Exhaust gas conduit 16 typically communicates the exhaust gas stream with catalytic reactor means and sound muffler means, not shown. A fuel metering and delivery device 18, which may be for example a fuel injection system or a carburetor, is illustrated schematically communicating with the intake end of intake manifold 12. Fuel metering and delivery device 18 is provided with an air cleaner 20 such that air ingested by engine 10 through intake manifold 12 may be drawn from the atmosphere through air cleaner 20 and through at least a portion of the fuel metering and delivery device 18. The construction, purpose and operation of the structure mentioned above is well known and further description is considered to be unnecessary.

Fuel metering and delivery device 18 is also provided with an air/fuel ratio modulator means 22. Air/fuel ratio modulator means 22 may be for example, in the case of an electronic fuel injection system, a variable resistor arranged to control the quantity of fuel delivered to engine 10 in relation to a given quantity of air or, in the case of a carburetor, may be a variably positionable metering valve arranged to control the quantity of fuel metered to engine 10 in respect of a given quantity of air. The air/fuel ratio modulator means 22 alternatively may be arranged to control a variably positionable air valve so that the quantity of air ingested by engine 10 in respect of a given quantity of fuel delivered by fuel metering and delivery device 18 may be modulated.

Exhaust gas conduit 16 is provided with an exhaust gas sensor 24 which is mounted on a suitable land or boss on conduit 16 so as to expose an exhaust gas chemistry responsive sensing element to the exhaust gases flowing through conduit 16. As used throughout this description, "exhaust gas sensor" is intended to mean a device or apparatus connected to an exhaust system for responding to the chemical constituents of the exhaust gases and which includes a solid ceramic wafer or chip with an electrical resistance which varies in response to variations in a chemical constituent of the exhaust gases which, in turn, varies directly with, and as a result of variations in the air/fuel ratio of the combustion mixture which produces the exhaust gases as a by-product of combustion. Exhaust gas sensor 24 communicates with electronic control means 26 through a pair of sensing leads 28, 30. Electronic control means 26 also communicates with the air/fuel ratio modulator means 22 through conductive contoller leads 32, 34. As described hereinbelow with reference to FIG. 4, the electronic control means 26 may be arranged to respond to changes in the exhaust gas chemistry which are sensed by exhaust gas sensor 24 to provide control signals for receipt by the air/fuel ratio modulator means 22 which control signals may be arranged to modulate either the air or the fuel content and hence the air/fuel ratio of the combustion mixture being provided to internal combustion engine 10 to thereby maintain a desired exhaust gas chemistry. It will be appreciated that the exhust gas sensor 24 could also be mounted on a suitable land or boss on exhaust manifold 14 with the mounting location being selected as a function of accessibility, temperature and convenience.

Figure 2:
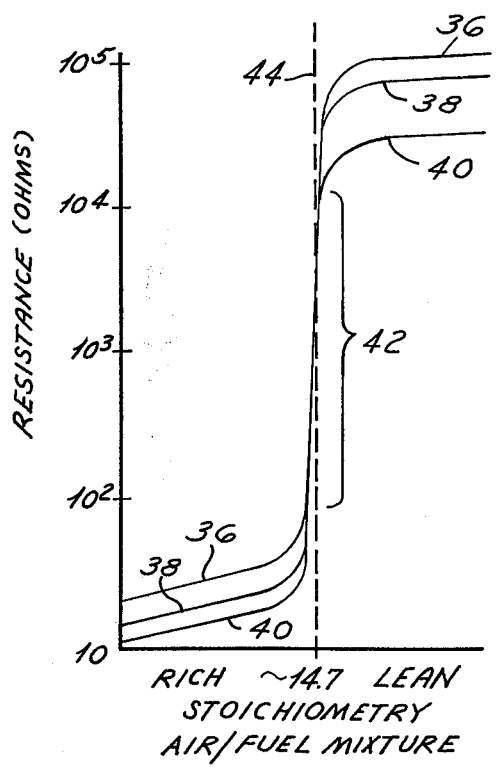
FIG. 2 is a graph which illustrates representative resistance versus air/fuel ration mixture curves. These curves typify the electrical behavior of the variable resistance exhaust gas chemistry responsive materials.

Referring now to FIG. 2, three resistance versus air/fuel ratio curves are graphed to illustrate the resistance response of a representative variable resistance exhaust gas chemistry responsive material at three different operating temperatures. The curves are identified as 36, 38 and 40 with curve 36 being the lowest temperature resistance curve and curve 40 being the highest temperature resistance curve. In the region denoted by numeral 42 it can be seen that the curves generally overlap and are nearly vertical. In each instance this corresponds approximately with the vertical line 44 which is indicated as an air/fuel ratio of 14.7 and is here intended to be indicative of stoichiometry. This region of overlap represents a significant change of resistance as can be seen but corresponds to a change in air/fuel ratio of only about ± 0.1 air/fuel ratios. The specific air/fuel ratio for stoichiometry will be a function of the chemical composition of the particular fuel mixture being used and in normally available gasolines may range from approximately 14.6 to approximately 14.8.

Exhaust gas catalysts are known which will promote or facilitate the rearrangement of the combustion by-product gases to produce water vapor and carbon dioxide. The catalysts which operate as three-way catalysts (i.e., which will reduce oxides of nitrogen and concomitantly oxidize hydrocarbons and carbon monoxides) require that the combustion by-product gases be produced by combustion of a stoichiometric air/fuel ratio. It will therefore be appreciated that maintenance of a stoichiometric air/fuel ratio is greatly to be desired and that, since the stoichiometric ratio may vary depending on the specific chemical formula of the fuel, frequent readjustment of the fuel metering and mixing device 18 is necessary. Since the region 42 substantially coincides with the stoichiometric ratio, the exhaust gas sensor 24 and electronic control means 26 may automatically adjust the air/fuel ratio modulator means 22 to vary the actual air/fuel ratio so as to coincide with the stoichiometric ratio for the particular fuel utilized as well as to accommodate other system variations.

The curve 36 corresponds with the resistance variation observed in an exhaust gas chemistry sensor subjected to a transition of combustion mixture ratios from the rich (fuel in excess of that required for complete combustion in a given quantity of oxygen) to the lean (oxygen in excess of that required for complete combustion of a given quantity of fuel) at relatively low elevated temperature, for example about 500°C. The resistance curve 40 corresponds to a resistance change which occurred under similar operating conditions at higher elevated temperature conditions, for example for about 900°C. Curve 38 represents a similar transition for an intermediate temperature. The range of temperatures expected to occur in a typical exhaust system ranges from the lowest elevated temperature at which the exhaust gas sensor would function, about 400°C, to a maximum temperature of about 1000°C. All curves were generated using the same fuel, one having a stoichiometric air/fuel ratio of 14.7. It can be seen that for both the high temperature and the low temperature transitions, a resistance change substantially in excess of two orders of magnitude occurs with an air/fuel ratio transition from slightly rich to slightly lean. It will therefore be appreciated that the exhaust gas sensor 24 may readily be arranged to maintain the actual air/fuel ratio at, or very close to, the stoichiometric ratio by attempting to modulate that ratio and maintain its own internal resistance at a value which approximates a selected point, for example the middle, of the range identified by numeral 42.

Referring now to FIG. 3, a sectional view of the exhaust gas sensor 24 according to the present invention is illustrated. Exhaust gas sensor 24 is comprised of a metallic outer body 50 and a ceramic insert member or insulator means 52. Ceramic insert member 52 is provided with a first forwardly extending portion 54 and a second rearward portion 56. First portion 54 is here shown to be conical and is provided with a wafer support slot 58 at the small end of the conical portion. First portion 54 is also provided with a pair of passages 60, 62 which extend rearwardly away from slot 58. A wafer 64 of exhaust gas responsive ceramic material is received and supported within slot 58. A pair of extending electrical leads 66, 68 extend away from wafer 64 and are received within passages 60 62. As a matter of convenience in describing positional relationships, "forward" refers to a direction toward wafer 64 and "rearward" refers to a direction away from wafer 64.

With reference to FIGS. 3 and 6, the forward face of ceramic insert member 53 is provided with counter-bore 70. Counter-bore 70 is aligned with and substantially co-extensive with slot 58 both of which extend to a depth (rearward from the face 72) greater than the comparable dimension of wafer 64. Thus, wafer 64 may be received within slot 58 to a depth which will permit walls 74 of counter-bore 70 to operate as shield means to protect the fragile wafer 64 from direct impingement of the pressure pulses of the exhaust gas stream while allowing counter-bore 70 to communicate the gaseous exhaust gas constituents to the wafer 64. The ceramic material of ceramic insert member 52 may readily be formed of a ceramic material sufficiently resistant to the exhaust gas environment to achieve the desired operating life.

Second portion 56 of the ceramic insert member 52 is provided with a second pair of passages 76, 78 which extend from the rear face 80 of the ceramic insert member 52 and which are positioned to intersect the passages 60, 62 at a location intermediate the forward face 72 and the rear face 80. Passages 60, 62 are sized to receive wafer leads 66, 68 in a loose fit condition. Passages 60, 62 should be sufficiently closely matched to the size of wafer leads 66, 68 to provide lateral support as will be described hereinbelow and may be for example of a diameter approximately 10 percent larger than the diameter of the wafer leads 66, 68. Passages 76, 78 are arranged to be substantially larger than passages 60, 62 and are positioned to intersect passages 60, 62.

A pair of generally rigid conductive connector pin members 82, 84 are illustrated as being received within passages 76, 78. Pin members 82, 84 are provided with connector terminal portions 86, 88 and these connector terminal portions are arranged to extend rearwardly from rear face 80. Conductor pins 82, 84 are provided with abutment shoulders 90, 92 which are in contact with rear face 80 following assembly to control insertion depth. Connector pins 82, 84 also include extending insert portions 94, 96 which may be conveniently of generally circular cross section and of a size which closely approximates the diameter, but of course is smaller than, passages 76, 78 to facilitate assertion therein. Forwardly extending portions 94, 96 are of a length measured from abutment shoulders 90, 92 which is slightly less than the depth of enlarged passages 76, 78 measured from rear face 80. For example, the presently preferred difference is about one-quarter of an inch.

With reference to FIGS. 3 and 5, and particularly with reference to FIG. 6, one of the features of the instant invention is illustrated. Wafer leads 66, 68 are shown to be extending through passages 60, 62 such that a short length of each of the free ends of the wafer leads 66, 68 extends into the forward portion of enlarged passages 76, 78. The free ends of wafer leads 66, 68 are bent over or crimped to extend generally transverse to the axes of passages 60, 62. This bending or crimping facilitates retention of wafer 64 within slot 58 during assembly. This also avoids interference between connector pins 82, 84 and wafer leads 66, 68 during assembly. The void between the forward portions of connector pins 82, 84 and the rearward portions of wafer leads 66, 68 is filled by conductive glass seal material 98, 100. As used herein "glass seal material" means a glass material, such as a borosilicate glass, selected to have a coefficient of thermal expansion which matches as closely as possible the coefficient of thermal expansion of the connector pins 82, 84 and the material of ceramic insert member 52, which has a softening temperature which exceeds about 1400°F., and which includes a quantity of metal powder or flake to achieve a resistance of less than about one ohm (1 $\Omega$) between the connector pins 82, 84 and wafer leads 66, 68 when assembled. The presently preferred ceramic material is a high alumina content ceramic material having a coefficient of thermal expansion of about $8.3 \times 10^{-6}$ inches per inch degree C measured from 0° to 1000°C. The presently preferred glass material is designated ES-1 by, and is available from, Kimble Glass Corporation. The metal conductor material is added as flakes of copper in a quantity to produce about 30% metal flake, about 60% glass and about 10% binders, resins and other volatile additives. As shown in FIG. 6, the glass seal material surrounds the forward portions of connector pins 82, 84 and the rearward, bent, portions of wafer leads 66, 68 and provides a low resistance conductive bridge therebetween.

Referring now to FIG. 4, the electrical controller means 26 is illustrated in a specific circuit embodiment. This circuit embodiment is merely illustrative and a large number of other circuit arrangements would be applicable for use with the exhaust gas sensor construction according to the invention.

A source of electrical energy, such as battery 102, is provided to energize the circuit. Battery 102 is arranged to have its negative terminal connected to the ground or common conductor 104, as is normally the case in domestic manufacture automobiles. The positive terminal of battery 102 is connected through switch 106 to a high voltage conductor 108. Switch 106 may be, for example, a portion of the ignition switch of the vehicle in which internal combustion engine 10 is installed. Exhaust gas sensor 24 is shown to be electrically communicated to the high voltage conductor 108 by one of the conductor pins 82, 84 while the other of the conductor pins 82, 84 communicates exhaust gas sensor 24 with a junction 110. Resistor 112 communicates junction 110 with the ground 104. A pair of variable potentiometers 114, 116 are arranged in parallel between the high voltage conductor 108 and the ground 104. The voltage tap 118 of variable potentiometer 114 is connected to one input terminal of voltage comparator 120 while the voltage tap 122 of variable potentiometer 116 is connected to one input terminal of voltage comparator 124. The voltage taps 118, 122 are connected to input terminals of opposite polarity such that, for example, voltage tap 118 is connected to the negative polarity input terminal of its associated voltage comparator 120 while voltage tap 122 is connected to the positive polarity input terminal of its associated voltage comparator 124. Junction 110 is communicated to the remaining two input terminals of the voltage comparators 120, 124.

As illustrated, the comparators 120, 124 are of the type having an internal output transistor which is either conductive or nonconductive depending on the character of the inputs applied to the comparator. If a potential applied to the positive input terminal of such a comparator is higher than the potential applied to its negative input, then the internal output transistor is rendered nonconductive and the associated pull-up resistor 126, 128 will apply substantially the potential of high voltage conductor 108 to the output terminal 130, 132 thereof of the respective comparator 120, 124. If the negative input of such a comparator is higher in potential than the potential applied to its positive input terminal, then the internal output transistor is rendered conductive and the voltage on the output lead thereof will be at substantially the ground potential.

With reference now to FIGS. 2 and 4, the operation of the circuit of FIG. 4 in association with the sensor according to the present invention will be explained. A representative resistance value is selected from the curves of the FIG. 2 graph. For example, a resistance value of 1200 $\Omega$ may represent the selected operating point within the range 42. Resistor 112 is selected to have a value such that the voltage appearing at junction 110 will be a predeterminable known quantity when the resistance of the sensor wafer 64 is at the selected point in range 42. By way of example, resistor 112 may be selected to be a 1200 $\Omega$ resistor so that, under design conditions, the voltage at the junction 110 will be one-half of the supply voltage of battery 102. This sensor voltage at junction 110 will be applied to the positive input terminal of comparator 120 and to the negative input terminal of comparator 124.

Variable potentiometer 114 may have its center tap 118 adjusted to apply a voltage to the negative input terminal of comparator 120 which is slightly more positive than the voltage calculated to appear at junction 110 when the combustion mixture supplied to the associated engine is at the value corresponding to the selected point in range 42 and therefore may represent the maximum permissible drift of the air/fuel ratio of the combustion mixture into the rich region. Variable potentiometer 116 may have its voltage tap 122 adjusted to apply a voltage at the positive input terminal of voltage comparator 124 to be slightly less than the voltage appearing at junction 110 under conditions corresponding to operation of the engine at an air/fuel ratio corresponding to the selected resistance value of sensor 24 within the range 42. This may therefore control the maximum drift of the air/fuel ratio into the lean region. Therefore, so long as the combustion mixture is being provided to the engine at, or very close to, the air/fuel ratio corresponding to the selected resistance value of the sensor wafer 64 the voltage comparators will be biased to an off and nonoperative condition. Lack of a signal appearing at ouput terminals 130, 132 may therefore operate to maintain the air/fuel ratio modulator means 22 in a static condition and the air/fuel ratio of the combustion mixture being provided to the engine will not vary. If for some reason the fuel content of the combustion mixture increases (a rich air/fuel mixture), the resistance of the sensor 24 will decrease and the voltage appearing at junction 110 will increase. When this increase is sufficiently large to indicate that the air/fuel ratio has drifted into the rich region beyond that point for which operational drift is permitted, as established by the set point of variable potentiometer 114, voltage comparator 120 will generate a high voltage which may represent an output signal. Such a signal maay initiate change of, or may be used to directly modulate, the setting of the air/fuel ratio modulator means 22 to begin to decrease the fuel content of the combustion mixture. As fuel content decreases, the resistance of the sensor wafer 64 will increase to the point that the voltage appearing at junction 110 will decrease to eventually remove any voltage signal at terminal 130.

If for some reason the fuel content of the combustion mixture decreases, the sensor resistance will begin to increase and comparator 124 will generate an output signal at terminal 132 to initiate an increase in the fuel content of the combustion mixture. Similarly, if the stoichiometric point should shift as a result of a difference in the chemical composition of the specific fuel being utilized, the shift will produce an increase or decrease in the resistance value of the wafer 64 resulting in a control signal to increase or decrease the fuel (or air) content or the air/fuel ratio. The combustion mixture will therefore be automatically adjusted to result in a stoichiometric mixture being provided to the engine 10. It will be appreciated that selection of components for the controller 26 will depend in large part upon the nature of the control electronics and upon the exact form of air/fuel ratio modulator means 22. If the air/fuel ratio modulator means 22 requires a certain form a signal (for example a high current or ground voltage signal), the comparator means 120, 124 may be selected accordingly with other component values being dictated thereby.

In assembly of the exhaust gas sensor 24 according to the present invention, a wafer 64 formed of an exhaust gas chemistry responsive ceramic such as, for example, described in U.S. Pat. No. 3,886,785, is prepared to have a pair of extending sensor leads 66, 68. Typically, these leads are fabricated from a noble metal conductor such as platinum to provide for the maximum in electrical conductor characteristics while preventing any co-reaction between the metal of the conductor and the ceramic of the wafer 64. A ceramic insert member 52 is fabricated from for example an alumina ceramic material and is arranged to have the forwardly extending first portion 54 with the second or rearward portion 56 and a plurality of passages 60, 62 and 76, 78 which intersect interiorly thereof at a point which is intermediate the counter-bored and slotted end 58 and the rear face 80. Sensor lead 66, 68 are inserted in the passages 60, 62 provided therefor and wafer 64 is seated within slot 58. In normal circumstances, slot 58 will be of approximately the same width as is the thickness of wafer 64 and will support, without interfering with, or applying clamping pressure the wafer 64 and without the use of cement. Alternatively, a ceramic cement could be utilized. With the wafer leads 66, 68 inserted within passages 60, 62 and wafer 64 supported within the slotted and counter-bored end portion, a pair of piston members are inserted with enlarged passages 76, 78 from the rear face 80 to crimp or bend the remote free ends. This bending or crimping will assist in retaining wafer 64 within slot 58 during succeeding manufacturing steps. The insertion of wafer 64 within the counter-bore 70 to a depth greater than the comparable dimension of wafer 64 will permit the loading force developed by the crimping pistons to be absorbed by ceramic body 52. The glass seal material 98, 100 is thereafter placed within enlarged passages 76, 78 in powder, bead or pellet form. The ceramic insulator means 52 thereafter is subjected to heating to elevate the temperature of the glass seal material 98, 100 to the softening temperature of the glass and is exposed to this temperature for a period of time sufficient to permit the glass seal material 98, 100 to become flowable. When the glass seal material has become flowable, connector pins 82, 84 are inserted into enlarged passages 76, 78 to bring the abutment shoulders 90, 92 come into contact with rear face 80. I have found that it is not sufficient to have simple contact between the forward ends of connector pins 82, 84 and the glass seal material 98, 100 but rather that the pins 82, 84 must be inserted into the molten glass seal material 98, 100 under force sufficient to cause some of the material to flow rearward around pins 82, 84 for a short distance and forward, through passages 60, 62 for a short distance around wafer leads 66, 68. To this end, the volume quantity of glass seal material must be slightly greater than the empty volume between the forward ends of pins 82, 84 and the forward ends of passages 76, 78. I believe that forcible insertion accomplishes two objectives. Firstly, the contact area between the pins 82, 84 and the glass seal material 98, 100 and between the glass seal material 98, 100 and the wafer leads 66, 68 is increased. Secondly, an ordering or alignment of metal particles within the glass seal material is thought to occur thereby providing a large number of conductive paths between the pins 82, 84 and the wafer leads 66, 68.

After the pins 82, 84 have been forcibly inserted into the enlarged passages 76, 78 of ceramic insert member 52, the ceramic insert member 52 can be provided with a suitable seal member or members situated within a gasket seat or seats provided therefor on a shoulder of the second portions of the insert member 52, as shown at 101 and the ceramic insert member 52 may be inserted within the outer metallic housing body 50. By the application of crimping pressure to the rear surface of the outer metallic body a unitary exhaust gas sensor device may be fabricated. In those instances where sufficient seal pressure is not available a second seal element can be used at a rear face of the ceramic insulator body.

It would be appreciated that the instant invention readily accomplishes its stated objectives. A one-piece ceramic insert member may be utilized while accomplishing the electrical interconnection between the wafer leads and the connector pin members at a point which is generally interior to, an intermediate the opposite ends of, the ceramic insulator member. By utilizing a conductive glass seal element, selected to be thermally compatible with the ceramic material, a good gas-tight seal can be formed to close off the passages which extend through the ceramic device and the glass seal material will have a viscosity characteristic which is compatible with the temperature to which the exhaust gas sensor 24 is to be exposed.

I claim:

1. An improved partial pressure of oxygen sensor for insertion in the exhaust system of an internal combustion engine comprising in combination:

housing body means;

a ceramic insulator means received within said housing body and having a slotted end portion, an oppositely positioned rear face, a first pair of generally parallel passages extending from said slotted end portion toward said rear face, and a second pair of generally parallel passages having a relatively larger diameter than said first pair of passages extending forward from said rear face and arranged to intersect said first pair of passages;

a wafer of partial pressure of oxygen responsive ceramic material received within said slotted end portion and having a pair of leads connected to said wafer in spaced apart relation and extending from said wafer through said first pair of passages;

a pair of pin means received within said second pair of passages; and glass seal material disposed at the forward interior portion of each of said second pair of passages for providing electrical communication between selected ones of said wafer leads and selected ones of said pin means and for sealing in gas tight fashion said first and second pairs of passages.

2. The sensor according to claim 1 wherein said pin means and said wafer leads are arranged to be noncontacting and said glass seal material is in a quantity in excess of that required to completely fill the forward portion of said enlarged passages between said pin means and said first pair of passages.

3. The sensor according to claim 1 wherein said ceramic body slotted end portion includes a counter-bore having a depth sufficient to completely receive said wafer, said counter-bore having an axis substantially parallel to said first pair of passages and coinciding with the slot of said slotted end portion, said first pair of passages intersecting said slot.

4. The sensor according to claim 3 wherein said ceramic body means comprises a generally cylindrical one-piece body of ceramic material having an expanded diameter central portion arranged for cooperation with said body means to retain said ceramic body means within said housing body means.

5. The sensor according to claim 4 wherein said first and second pairs of passages intersect within said expanded diameter central portion.

6. The sensor according to claim 1 wherein said glass seal material comprises an electrically conductive glass having a softening point above about 1400°F.

7. The sensor according to claim 6 wherein said glass seal material is rendered conductive by the inclusion therein at least about 30% of particles of conductive metal.

8. An improved partial pressure of oxygen sensor for insertion in the exhaust system of an internal combustion engine comprising in combination:
- housing body means;
- a ceramic insulator means received within said housing body means and having a forwardly extending, slotted, end portion, an oppositely positioned rear face and a first pair of generally parallel passages extending from said slotted end portion rearward;
- said slotted end portion having a counter-bore extending generally parallel to said first pair of passages, the axis of the counter-bore coinciding with the slot;
- a wafer of partial pressure of oxygen responsive ceramic material received within the slot of said slotted end portion to a depth which exceeds the height of said wafer whereby said wafer may be protected from direct impingement of pressure pulses;
- said wafer having a pair of leads connected thereto in spaced apart relation and extending from said wafer through said first pair of passages;
- electrical means communicating said wafer leads to utilization means; and
- seal means to seal said wafer leads in said first pair of passages in gas tight fashion.

9. The sensor according to claim 8 wherein said ceramic body means comprises a generally cylindrical one-piece body of ceramic material having an expanded diameter central portion arranged for cooperation with said body means to retain said ceramic body means within said housing body means.

10. The sensor according to claim 9 including a second pair of generally parallel passages extending forwardly from said rear face, having a diameter enlarged with respect to said first pair of passages, and arranged to intersect said first pair of passages within said expanded diameter central portion.

* * * * *